United States Patent [19]

Fischell

[11] Patent Number: 4,596,242
[45] Date of Patent: Jun. 24, 1986

[54] METHOD AND APPARATUS FOR ACHIEVING PENILE ERECTION IN A HUMAN MALE

[76] Inventor: Robert E. Fischell, 1027 McCeney Ave., Silver Spring, Md. 20901

[21] Appl. No.: 526,893

[22] Filed: Aug. 26, 1983

[51] Int. Cl.⁴ ............................................. A61F 5/00
[52] U.S. Cl. ................................. 128/79; 128/DIG. 25
[58] Field of Search ............... 128/79, 1 R, DIG. 25; 604/141

[56] References Cited

U.S. PATENT DOCUMENTS

| | | | |
|---|---|---|---|
| 3,731,681 | 5/1973 | Blackshear et al. | 604/141 |
| 3,954,102 | 5/1976 | Buuck | 128/79 |
| 4,299,220 | 11/1981 | Dorman | 604/141 X |
| 4,342,308 | 8/1982 | Trick | 128/79 |
| 4,437,457 | 3/1984 | Trick et al. | 128/DIG. 25 |

Primary Examiner—Dalton L. Truluck
Attorney, Agent, or Firm—Sachs & Sachs

[57] ABSTRACT

A method and apparatus for achieving penile erection in a human male. The apparatus includes at least one distensible cylinder which is in communication with pressure reservoir means through a valve means. A fluid pressure generator acts upon a working fluid in the pressure reservoir means and when the valve means is opened, the distensible cylinder distends. The method concerns implantation and use of the apparatus.

36 Claims, 7 Drawing Figures

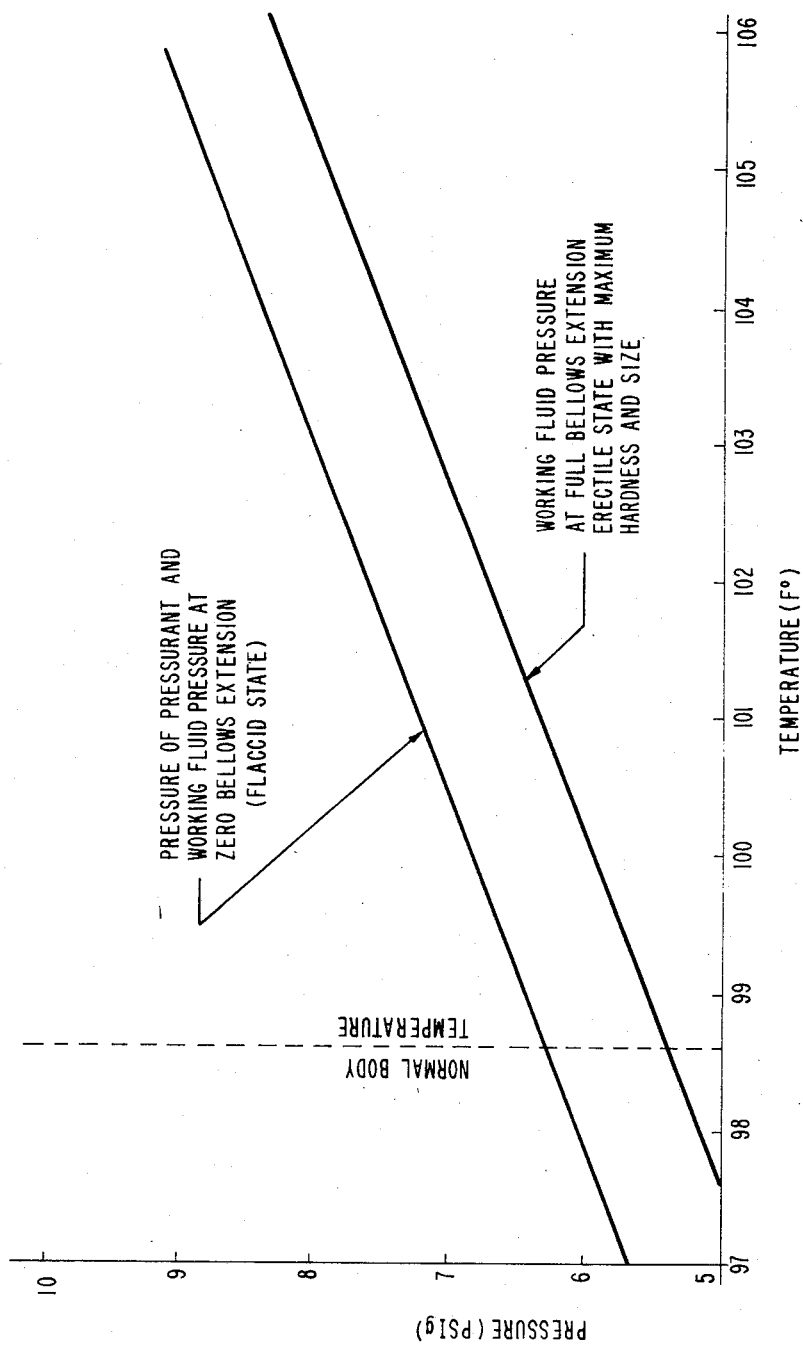

METHOD AND APPARATUS FOR ACHIEVING PENILE ERECTION IN A HUMAN MALE

BACKGROUND OF THE INVENTION

1. Field of the Invention

This invention relates to an improved, manually actuated, hydraulic device to provide a penile erection for human males who suffer the dysfunction of erectile impotence.

2. Description of the Prior Art

The normal male achieves an erection when a multitude of small blood vessels within a long cylindrical section on each side of the penis called the corposum cavernosum fills with blood as a result of an increase in the vessels' output resistance to blood flow. There are two such parallel cylinders in the penis (the plural being the corpora cavernosa) which simultaneously become engorged with blood, thereby producing a penile erection. Unfortunately, there are 10 million men, in the United States alone, who are unable to achieve a penile erection.

There are many causes for impotency in the human male, both psychological and physiological. Among the physiological causes are: long term diabetes, damage to the spinal cord, multiple schlerosis, a surgical procedure in the lower abdomen that has caused nerve damage in the genital region, and advanced age. Such impotence often destroys the male's psychological well being, and often seriously disrupts or even causes the dissolutionment of an otherwise fulfilling relationship. It is therefore not surprising to find that the patient art is replete with examples of artificial penile erection devices.

One of the earliest prosthetic devices whose object was to achieve a penile erection is described by Henderson in U.S. Pat. No. 1,133,958 (March 1915). This device suggests the use of an external truss to stiffen the penis by preventing the back-flow of blood. Since the truss is removable, it is a simple matter to obtain a normal flaccid state. However, the external truss mechanism also prevents in-flow of blood and, therefore, cannot provide the five conditions required of a normally erect penis; namely, during erection the penis should become longer, thicker, harder, stiffer, and having a generally upward angle.

Kalnberz, in U.S. Pat. No. 3,832,996 (September, 1974), describes two stiff rods designed to be implanted in the corpora cavernosa to attain a penile erection. Although this system provides a longer, thicker, and stiffer erectile state, it does not provide a generally upward angle, and the flaccid state is no longer achievable.

An improved rod is described by Barrington in U.S. Pat. No. 4,151,840 (May 1979), which rod provides a longer, thicker, and stiffer erect state. Furthermore, the device can be bent downwardly by hand to achieve the flaccid condition. However, in the flaccid condition, the penis is just as long and thick as in the erect state; also, it is unnaturally stiff and hard.

A manually actuated fluid driven system is described by Strauch et al in U.S. Pat. No. 3,853,122 (December 1974). One drawback in the Strauch et al system is that the required energy for moving the working fluid from the storage container or reservoir thereof must be obtained by manually squeezing the reservoir. Further, another difficulty is that fluid exits the region of the penis automatically through a metering means not under external control. The penis therefore could become flaccid too quickly, or could take an unreasonably long time to become flaccid, all depending upon the configuration of the metering means.

Furthermore, the Strauch et al invention requires a reservoir or fluid container that must be manually squeezed in order to drive fluid into the penile stiffener cylinder thereof. A disadvantage of this design is that if the container is large enough to hold a sufficient volume so as to cause an appreciable change in size between the erectile and flaccid states, then it is too large to be placed in the scrotum. If the fluid container is placed in the abdomen (where it must be located just under the skin so that it can be readily pushed on), it would be sufficiently large so as to cause some perceptible abdominal distortion, and would certainly be distinctly felt by the man in whom it was implanted.

Buuck, in U.S. Pat. No. 3,954,102 (May 1976), describes a manually actuated, fluid driven, inflatable penile prothesis with two cylinders in the corpora cavernosa. The Buuck prothesis achieves the erection goals of a longer, thicker, harder, and stiffer penis with a generally (though not certainly physiologically sufficient) upward angle during erection, and also provides a physiologically normal flaccid state. Furthermore, the Buuck invention overcomes one shortcoming of the Stauch et al invention in that it utilizes a large reservoir but that fluid container is placed deep inside the abdomen where it cannot be felt but where it can be operated remotely by a pump located in the scrotum. However, this device still has certain major shortcomings. For example, when the penis is in the erect state, its upward angle may not reach that achieved in a normal male. Further, the pump and release valve are located in the scrotum, which is one of the body sites most disposed to post-operative discomfort and infection. The Buuck device requires multiple strokes of the pump within the scrotum to achieve an erection, which could require one or more minutes of pumping, especially if the patient does not have the manual dexterity required for pumping a small bulb located within the scrotum. Furthermore, the release valve in the scrotum must be held for on the order of ten to fifteen seconds to return the penis to the flaccid state. Also, a comparatively large reservoir is required by Buuck because fluid cannot be added after implant without surgical intervention. As a consequence of the large reservoir and small displacement pump used by Buuck, it is possible to permanently distend or even rupture the stiffener cylinders by excessive pumping. Additionally, because of the many separate pieces of tubing and other parts required by the Buuck device it is necessary to fill and then assemble the many separate parts during the surgical implant. This is a time consuming and therefore costly procedure and can lead to leaking and broken connections.

A further element of the prior art is U.S. Pat. No. 4,009,711 (March, 1977), which issued to Uson, and which describes a non-distensible portion of a stiffener cylinder that is placed in the root of the corpus cavernosum, and a distensible portion that is located within the pendulous portion of the corpus cavernosum. Although there may be valid reasons to provide a structure such as that described by Uson, it is disadvantageous to have a considerable portion of the stiffener cylinder located within the root of the corpus cavernosum if it is not pliable and distensible. In this regard, some shortcomings of the Uson device are that the penis does not feel natural in the flaccid condition because there is a rigid object just beneath the skin at the base of the penis. Furthermore, the shape of the penis in the flaccid condition is not physiologically normal, nor is there stress relief provided for the elastomer stiffener cylinder during the flaccid state (which is most of the time) because the cylinder does not begin its downward curve while still supported within the root of the corpus cavernosum. Additionally, a greater extended length of the penis in the erect state cannot be achieved because the cylinder does not begin its extendible portion within the root of the corpus cavernosum.

A still further element in the prior art is U.S. Pat. No. 4,342,308 which was issued to Trick (August 1982), and describes an elongated cylindrical actuator for a penile erection device that, in one embodiment thereof, is suggested for implantation in the abdomen. However, the elongated shape of the Trick device (as opposed to a flat disc shape) is inappropriate for abdominal implant since it is bulky, yet must be close enough to the surface to be pushed through the skin in order to operate. Furthermore, the Trick device for abdominal implant requires a complex mechanism which is inherently less reliable as compared with the comparatively simple system of the subject invention. Furthermore, if the abdominal implant version of the Trick patent is inadvertently pushed during sexual activity, the penis will be prematurely returned to its flaccid state.

A still further disadvantage of both embodiments of the Trick invention is that they employ a spring which is used to develop the mechanical movement required to force a fluid to fill the penile stiffener cylinders. As is well known in engineering, the force exerted by a spring is proportional to its linear displacement. Thus, to obtain the full extent of the spring's linear displacement, the final fluid pressure will unacceptably approach zero. If the pressurized fluid is allowed to go over a comparatively large (say a factor of 2) change in pressure from full pressure to half pressure, then only half the displacement of the spring could be utilized. The use of the Trick device in this way would require a factor of two greater total volume of the reservoir as compared to the actual volume of fluid necessary to fill the penile stiffener cylinders. As an example, if the two stiffener cylinders were filled with a total volume of 50 milliliters of fluid at a pressure of 5 psi, then the Trick device might initially exert a pressure as high as 10 psi and at a half volumetric displacement of 50 milliliters would exert a pressure of 5 psi. But, this would still require a total reservoir volume for the Trick device of 100 milliliters, of which half that volume serves no useful purpose; and, as a matter of fact, causes the implanted reservoir to be twice as large as the minimum required to obtain the desired volumetric displacement of 50 milliliters.

The present invention overcomes the problems associated with the prior art by providing a method and a implantable apparatus for achieving penile erection in a human male which simulates normal psychological conditions, which can be totally implanted without providing perceptible psychological disadvantages which requires almost negligible under skin manipulation by the user, which does not require a complex mechanical structure, which does not prematurely or accidentally cause penile flaccidity, and which does not use supplied mechanical energy to obtain the erect state.

More specifically, the present invention, unlike several other inflatable penile devices, prevents the working fluid from gradually returning to the reservoir thereof as is taught by Strauch, et al (U.S. Pat. No. 3,853,122) or Yamanaka (U.S. Pat. No. 4,235,277), nor can it be inadvertently triggered by pressure on the abdomen during sexual activity as is the case with the Trick (U.S. Pat. No. 4,342,308) design. Also, no mechanical squeezing of a reservoir is required as in Strauch et al (U.S. Pat. No. 3,853,122), nor is pumping required, as in Buuck (U.S. Pat. No. 3,954,102). Furthermore, reliance on mechanical spring pressure as in Trick is eliminated.

SUMMARY OF THE INVENTION

It is, therefore, highly desirable to provide a simple, safe, reliable and easy to operate and comparatively inconspicuous implantable device whereby the impotent male can achieve a penile erection that is physiologically normal; i.e., the device should cause the penis to become longer, thicker, harder, and stiffer, and to assume a generally upward angle. It is further desirable to have the penis return to a normal, flaccid condition at all times other than during sexual activity. Ideally, these two physiologically normal operating characteristics should be achievable promptly on command of the individual in whom the device is implanted.

To this end, one object of the present invention is to provide a means for readily causing the penis to achieve an erect state which is physiologically equivalent to that of the normal male. Specifically, an object is to provide a device whereby the penis becomes longer, thicker, harder, stiffer, and attains a proper upward angle.

Another object of the invention is to provide a penile erection device having a readily achieved and physiologically normal flaccid state.

Yet a further object is to provide a penile erection device wherein the erect state can be achieved rapidly by a single push of a releaser valve located just beneath the skin of the lower abdomen without requiring pumping or manual squeezing of a reservoir containing the fluid that is to be displaced into the penile stiffener cylinders.

Another object is to provide a rigid reservoir containing a comparatively large fluid volume that is located deep into the abdomen where it is not readily able to be felt by the man or his sexual partner.

Another object of this invention is to provide a reservoir that can transfer essentially its entire fluid volume at an essentially constant pressure thus allowing use of a minimally sized reservoir that still provides the desired volumetric displacement.

Still another object of the invention is to provide a device wherein the flaccid penile state can be achieved rapidly by a single push of a releaser valve located just below the skin at the base of the penis while simultaneously squeezing the penis with the other hand or more slowly merely by squeezing the penis without pushing on the releaser valve.

A further object of the invention is to provide an effective, fully implantable device, wherein no part of the structure thereof is located in the scrotum.

Another object of the present invention is to provide a device wherein the reservoir is designed with a limited pressure capability so that the two stiffener cylinders located in the corpora cavernosa cannot be overpressurized.

Yet a further object of the invention is to provide a fully implantable penile erection device including means for postoperatively adjusting the fluid level within the device, without surgical intervention, for adjusting the erect and flaccid states.

Yet a further object of the invention is to provide a releaser to be located under the skin in the lower abdomen which has a flat, disc shape which is ideally suited for being operated by pressing through the skin.

Still another object of the invention is to provide a device which can be assembled and pre-filled prior to surgical implantation so that the time required for the surgical implant is reduced.

Yet a further object of the present invention is to provide a fully implantable penile erection device wherein the bottom shell of the releaser thereof is provided with at least one concave surface which improves implant positional stability when the device is actuated by pushing through the skin.

Yet a further object of the present invention is to provide an abdominal implant, manually actuated, penile erection device that will not inadvertently return the penis to the flaccid state if the releaser thereof is accidentally pushed during sexual activity.

These and other objects of the invention, as well as many of the attendant advantages thereof, will become more readily apparent when reference is made to the following description, taken in conjunction with the accompanying drawings.

In the broad sense, an implantable apparatus for implantation at a selected location in a body according to the principles of the present invention comprises: at least one distensible member for implantation, each of the at least one distensible members forming an internal chamber, each of the at least one distensible members being distensible when their respective internal chambers are pressurized; pressure reservoir means; valve means coupling the respective internal chambers of each of the at least one distensible members to the pressure reservoir, each of the at least one distensible members not being in communication with the pressure reservoir when the valve means is at rest, each of the at least one distensible members and the pressure reservoir being in communication when the valve means is opened; a working fluid being disposed in the pressure reservoir means and being transferable between the internal chambers of each of the at least one distensible members and the pressure reservoir means; and fluid pressure generator means for pressurizing the working fluid in the pressure reservoir means when the valve means is at rest, opening of the valve means causing a transfer of the working fluid from the pressure reservoir means to the internal chambers of each of the at least one distensible members.

More specifically, an implantable apparatus for achieving penile erection in a human male according to the principles of the present invention comprises: at least one distensible cylinder for implantation in one of the corpora cavernosa of the penis of the human male, each of the at least one distensible cylinders forming internal chambers, each of the at least one distensible cylinders being distensible when the respective internal chambers are pressurized; pressure reservoir means; valve means coupling the respective internal chambers of each of the at least one distensible cylinders to the pressure reservoir, each of the at least one distensible cylinders not being in communication with the pressure reservoir when the valve means is at rest, each of the at least one distensible cylinders being in communication with the pressure reservoir when said valve means is opened; a working fluid being disposed in the pressure reservoir means and being transferable between the internal chambers of each of the at least one distensible cylinders and the pressure reservoir means; and fluid pressure generator means for inherently pressurizing the working fluid in the pressure reservoir means when the valve means is at rest, opening of the valve means causing a transfer of the working fluid from the pressure reservoir means to the internal chambers of each of the at least one distensible cylinders.

A method for permitting a human male to selectively achieve a penile erection in accordance with the principles of the present invention comprises the steps of: implanting in a human male first and second distensible cylinders, respectively, in the two corpora cavernosa of the penis of the human male, the distensible cylinders being distensible when supplied internally with a pressurized working fluid; and simultaneously implanting in the human male a pressure reservoir and pressure means for inherently pressurizing a working fluid in the pressure reservoir, the distensible cylinders being in communication with the pressure reservoir through an also simultaneously implanted valve means; opening of the valve means causing flow of the working fluid from the pressure reservoir to the interiors of the distensible cylinders so as to cause a pressure increase therein and distension of the distensible cylinders.

BRIEF DESCRIPTION OF THE DRAWINGS

FIG. 3 graphically illustrates the pressure within the reservoir as a function of body temperature.

DESCRIPTION OF THE PREFERRED EMBODIMENTS

Described herein is a manually actuated penile erection device wherein the pressure driving the fluid into the stiffener cylinders originates from the vapor pressure of a fluid contained within a bellows contained within a rigid reservoir, as hereinafter described.

Figure 1:
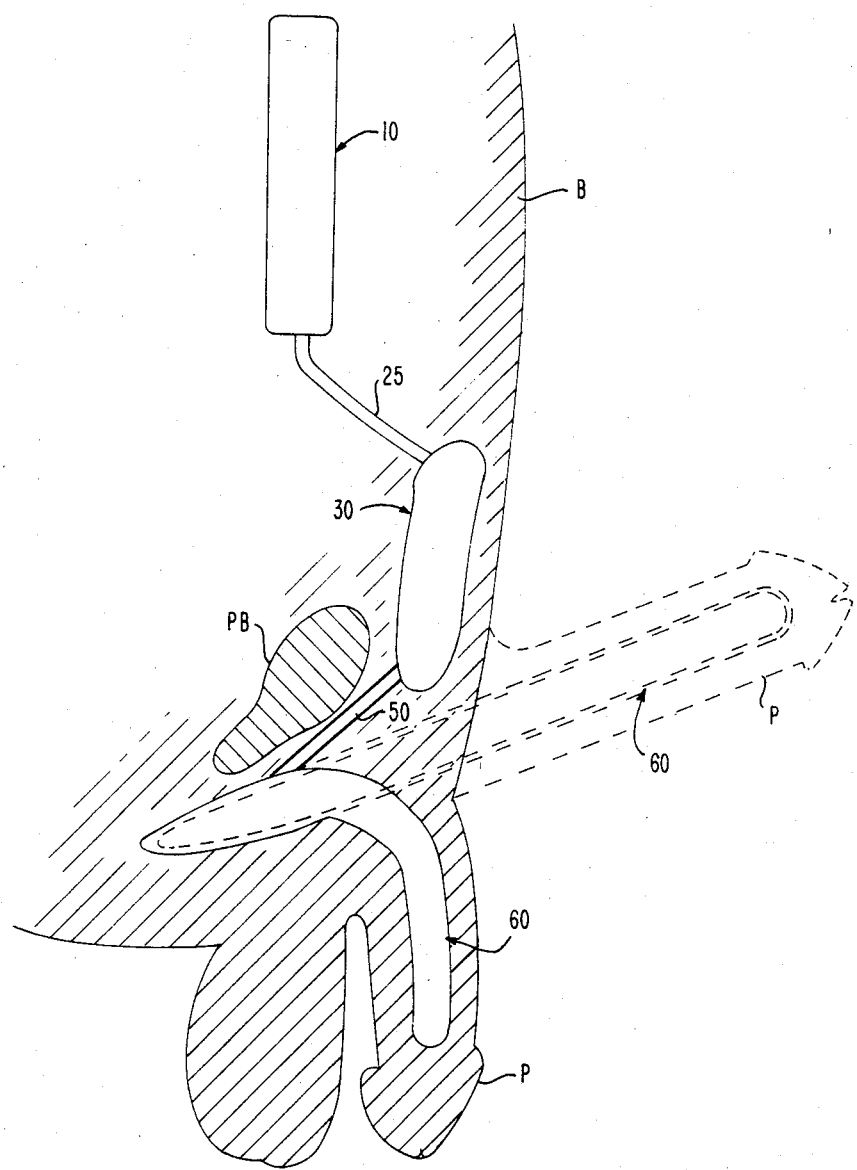
FIG. 1 is a side view of a fully implantable vapor pressure driven penile erection device, constructed in accordance with the principles of the subject invention, showing the various elements of the device and showing the penis in both the flaccid and the erect states.

FIG. 1 shows the major elements of this system implanted for use. A reservoir 10 of a comparatively large fluid volume is located deep within a body B where it is minimally perceptible. This is in contrast to a location closer to the surface of the skin which would be necessary if the reservoir 10 needed to be readily manipulated. The reservoir 10 is preferably rigid and does not have any exterior flexible surface. The reservoir 10 is connected by a flexible tube 25 to a manually actuated releaser 30 which in turn is connected through two comparatively rigid connecting tubes 50 to two hollow stiffener cylinders 60 each located in the penis P. Only one tube 50 and one stiffener cylinder 60 is shown, but these are of the same construction and therefore are representative of the others, not illustrated. The releaser 30 is essentially a valve, as hereinafter described, and selectively places the interior of the reservoir 10 in communication with the interior of the stiffener cylinders 60 via the tubes 25 and 50.

The two tubes 50 are preferably implanted such that they pass just anterior to the public bone PB and are sufficiently stiff to help provide a generally upward angle to the penis in the erect state. The penile erection device is employed to provide an otherwise impotent human male with an essentially immediate penile erect state (as shown by the phantom lines of FIG. 1) or a flaccid state (as shown by solid lines) whenever such states are desired by that person. Since reservoir 10, containing all the fluid that will be displaced into the cylinders 60, can be located so deeply within the abdomen, it is not discernible to the patient or to his sexual partner. The reservoir 10 is preferably constructed of titanium or like biocompatible material.

Furthermore, this reservoir 10 can have a great volume, while remaining unnoticed by the patient, because it is implanted deeply in the abdomen. A great volume in the reservoir allows for a greater variation in the volume of the stiffener cylinders 60 between the erect and flaccid states, thus allowing much larger erect states for the same physiologically normal flaccid state. For example, the reservoir 10 could have a volume of 50 milliliters, a much greater volume than could be conveniently placed within the scrotum.

The two hollow stiffener cylinders are preferably constructed of medical grade silicone rubber and are implanted one in each corpus cavernosum, and are distensible throughout their entire length. This is illustrated in FIG. 1 by the thin wall of the stiffener cylinder 60 which is shown throughout its entire length, including the root portion. This construction allows the maximum distensibility of the entire stiffener cylinder and therefore the largest possible extension of the penis when the erect state thereof is desired.

Figure 2:
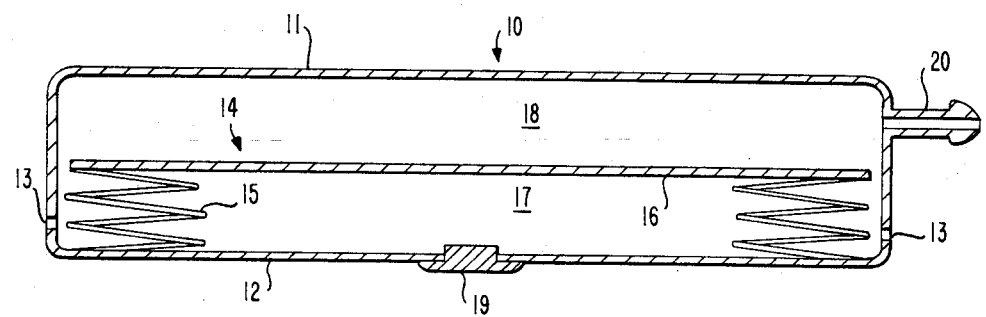
FIG. 2 is a cross-sectional view of the reservoir of the subject invention.

FIG. 2 illustrates a preferred embodiment of one component of this invention, specifically the vapor-pressure driven reservoir 10. A bellows 14 preferably of titanium or the like, is located within the preferably flat cylindrically shaped reservoir 10 which has a rigid upper shell 11 and a rigid lower shell 12 welded together at weld 13, both preferably being constructed of titanium or the like. The bellows 14 is closed ended and is formed of convolutions 15 welded at one end of the bellows 14 to the bottom shell 12 and welded closed at its other end to a top plate 16. A reservoir volume 18 is defined on the interior thereof and is situated exterior to the bellows 14. The reservoir volume 18 is filled with a typical working fluid, not illustrated, such as normal saline solution or a body compatible radio-opaque solution that is used to fill and inflate the stiffener cylinders 60. If radio-opaque solution is employed, leaks can be detected by X-ray and localized repairs can be effected without the necessity of additional surgery. Typical bellows characteristics are as follows:

Material: Grade 2, CP titanium (99.4% pure titanium)
Convolution Thickness: 0.05 millimeters (2 mils)
No. of Convolutions: 10
Outside Diameter: 7.62 centimeters (3 inches)
Inside Diameter of Convolutions: 6.35 centimeters (2.5 inches)
Stroke Length: 1.27 centimeters (½ inch)
Volume at Full Stroke: 50 milliliters
Compressed Height: 1.25 millimeters (50 mils)
Force to Extend to Full Stroke: 5 lbs.
Pressure to Extend to Full Stroke: 0.9 pounds per square inch (psi)

The bellows 14, as shown in FIG. 2, forms a pressurant chamber 17 therein for containing a pressurant fluid, not illustrated, such as 2-methylbutane, which changes state between liquid and vapor as the fluid level within the bellows 14 is varied, but always maintaining a constant pressure at constant temperature. The lower shell 12 contains a plug 19 that is welded in place to seal the pressurant into the pressurant chamber 17. At body temperature, the pressurant fluid maintains a pressure of approximately 6.3 pounds per square inch, gauge pressure (psig) (21.0 pounds per square inch, absolute (psia)) which is sufficient (but not excessive) for driving fluid into the penile stiffener cylinders. Thus, when the bellows 14 is in its unextended position, corresponding to the flaccid state of the penis, most of the pressurant fluid is in the liquid state and therefore the fluid pressurant chamber 17 occupies very little volume. When the bellows 14 is expanded (corresponding to the erect state) most of the pressurant fluid is in the vapor state thereby increasing the pressurant volume 17 but always imparting a positive pressure to the working fluid contained in the reservoir volume 18.

In fact, the pressure imparted to the working fluid depends on:
1. The type of pressurant used within the bellows, lows,
2. The temperature of the body (i.e., the temperature of the pressurant fluid) and,
3. The extent of the extension of the bellows, Considering these three factors, one of ordinary skill in the art can select different bellows and pressurant fluid combinations suitable to produce the desired result within the principles and scope of the present invention.

FIG. 3 shows the curve of pressure versus temperature for the preferred pressurant fluid, 2-methylbutane. It should be understood, however, that any pressurant (such as a fluorocarbon) could be used that provides pressures in the range of 1 to 20 psig at normal body temperature.

It can also be seen from FIG. 3 that the working fluid pressure is reduced by the pressure required from the pressurant for extension of the bellows. For a typical bellows as herein before described, this results in only a 0.9 psi reduction of working fluid pressure at full bellows extension. Thus the pressure of the working fluid changes only from 6.3 psig with the bellows fully contracted to 5.4 psig at full extension.

FIG. 3 shows that this system provides reasonable positive pressures for the working fluid for all extensions of the bellows and for all temperatures encountered by a living human body.

The present invention has the distinct advantage of displacing its entire working fluid volume at a nearly constant pressure. Thus 50 milliliters (as a designed volumetric displacement) can be obtained with essentially a reservoir volume of only that 50 milliliters, and a pressure change of only from 6.3 psig to 5.4 psig. Thus the present invention provides a minimum total volume for the reservoir.

An inlet/outlet tube 20 connects to the tubing 25 shown in FIG. 1 to communicate the working fluid from the reservoir 10, through the releaser 30 into the stiffener cylinders 60.

Figure 4:
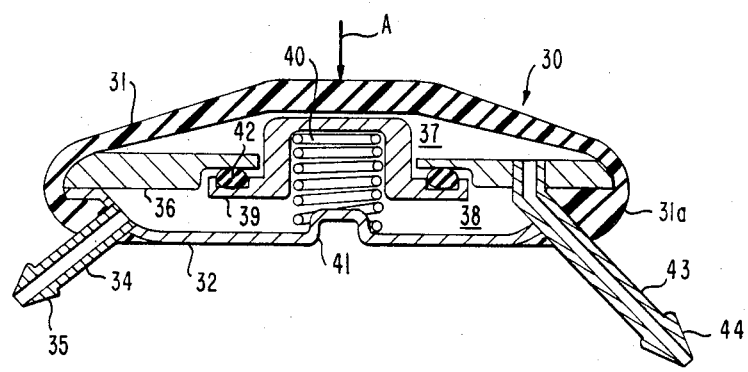
FIG. 4 is a cross-sectional view of the releaser of the present invention taken substantially through the lines 4—4 of FIG. 5.
Figure 5:
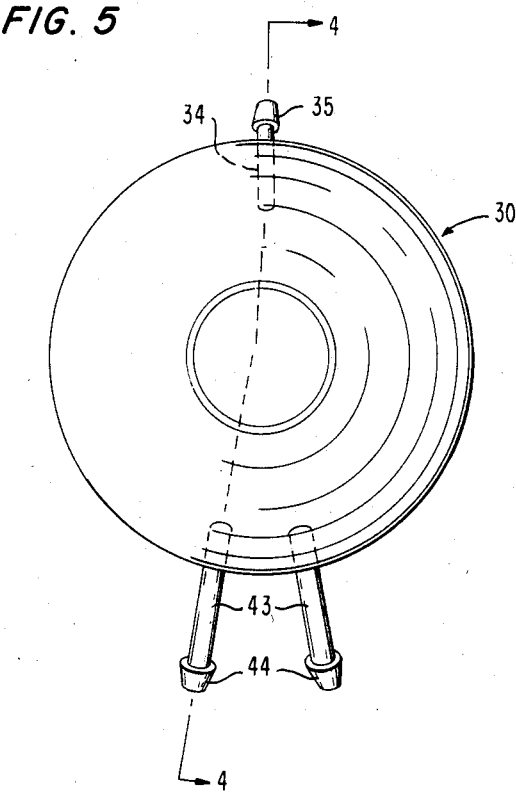
FIG. 5 is a plan view of the releaser.

FIG. 4 shows a cross-section of a cylindrically shaped releaser 30 having a diaphragm/septum 31 preferably of an elastomer mounted by a thick bead 31a onto a bottom shell 32 which is welded along its outer diameter to a base plate 36. FIG. 5 is a plan view of the releaser 30. The elastomer is preferably medical grade silicone rubber and the bottom shell 32 and base plate 36 are preferably made from an alloy being 90% titanium, 6% aluminum and 4% vandium, typically known as titanium alloy 6A14V. The releaser 30 preferably has an outer diameter of 2.5 inches. An inlet tube 34 of the releaser 30 has an increased diameter shoulder 35 which helps to secure the connecting tube 25 from the reservoir 10.

The base plate 36 has a central aperture disposed therethrough in which is reciprocally mounted a valve poppet 39, incorporating an "O"-ring 42. The valve poppet 39 is maintained in a normally closed position by a valve spring 40. Although valve spring 40 is shown as being of the helical type, it is to be understood that other suitable biasing means can be employed. Working fluid passing through the inlet tube 34 enters the lower chamber 38 of the releaser 30. The working fluid is normally prevented from leaking into the upper chamber 37 by the "O"-ring 42 which seats against the bottom surface of the base plate 36, and thus the flaccid state is normally maintained. When finger pressure is applied through the skin onto the top surface of the diaphragm/septum 31 as shown at "A", the valve poppet 39 will be depressed thus breaking the "O"-ring seal and thereby allowing working fluid to pass from the lower chamber 38 into the upper chamber 37 and eventually to the stiffener cylinders 60. Since the pressure in the reservoir 10 is always great enough to fully fill (but not overpressure) the cylinders 60, exerting a force at "A", which opens the poppet 39, will allow fluid to be driven from the reservoir 10, through the releaser 30, through the outlet tube 43 (having an enlarged diameter shoulder 44 to hold the tubing 50), through the connecting tubing 50, and then into the stiffener cylinders 60, thus causing the erect state to occur.

Unlike the invention described by Strauch et al, (U.S. Pat. No. 3,853,122) in the present invention, even the slightest displacement of the valve poppet 39 will allow essentially the full volume of the working fluid contained in the reservoir 10 to be displaced into the stiffener cylinders 60. If the fluid container (i.e., reservoir) described in the Strauch et al invention was given only this slight displacement, the result would be only a trivial and insufficient displacement of fluid which would not achieve the desired goal of causing the stiffener cylinders to become distinctly harder and preferably longer and thicker in diameter.

Returning now to FIG. 4, when finger pressure is removed from the poppet 39 the valve spring 40, mounted at its base to the centering cavity 41, will cause the poppet 39 to return to its normal rest position. The cavity 41 also provides a concave outer surface into which fibrous body tissue will grow thus helping to stabilize the position of the implanted releaser so that it is not dislodged from its implant site when pushed on through the skin.

Thus it can be seen that the present invention operates on a simple fundamental principle; namely, energy for moving the working fluid into the stiffener cylinders is stored as heat energy in the pressurant in contrast to prior art devices which require mechanical spring pressure or pumping. Manually pushing on the releaser poppet 39 (of FIG. 4) merely allows the release of the fluid so that the pressurant can drive that working fluid into the stiffener cylinders. In so doing, the pressurant fluid is cooled. Energy is restored to the pressurant by reheating it using heat energy from the body and also by the energy of compressing the pressurant when the penis is squeezed after sexual activity, as hereinafter described, thus compressing the pressurant in the pressurant volume 17 of the reservoir 10 as shown in FIG. 2. Essentially, then, one fluid is used to move another during the transition from the flaccid to the erect state or vice versa. The present invention, if inadvertently pushed at the releaser 30 during sexual activity, will not cause a deflation of the stiffener cylinders 60.

At the completion of sexual activity, the flaccid state is promptly restored by squeezing the penis with one hand thus forcing the fluid to return to the reservoir chamber 18 of the reservoir 10. Of course, the spring constant of the valve spring 40 must be selected so that the valve poppet 39 normally stays closed but will be forced open if the penis is directly and intentionally manually squeezed. The degree to which the penis is made smaller and softer in the flaccid state is adjustable by the extent to which the individual compresses his penis thus forcing fluid to return to the reservoir 10. This technique also allows the individual to adjust the hardness and size of the penis during the erect state. In this embodiment of the present invention, therefore the valve need not be touched in order to return the working fluid to the reservoir.

Figure 6:
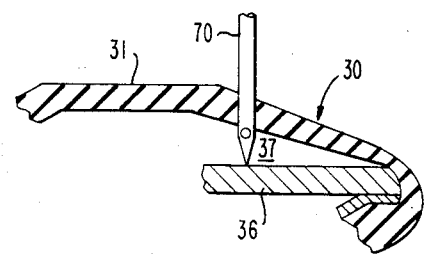
FIG. 6 is fragmentary cross-sectional view of the releaser of the subject invention and use of a non-coring hypodermic needle to penetrate the diaphragm/septum of the releaser for postopertatively adjusting fluid volume.

As shown in FIG. 6, the diaphragm/septum 31 of the releaser 30 can be penetrated by a Whitacre point (non-coring) hypodermic needle 70 that first penetrates the skin. A syringe connected to the needle can be used to add or delete fluid from the system, thus the flaccid and erect states are, to some extent adjustable after implant. By making the diaphragm/septum 31 of a comparatively soft rubber (such as medical grade silicone rubber, 40 durometer) and by making it comparatively thick (e.g. 2 millimeters), it will provide the desired characteristics of a self-sealing diaphragm/septum.

Figure 7:
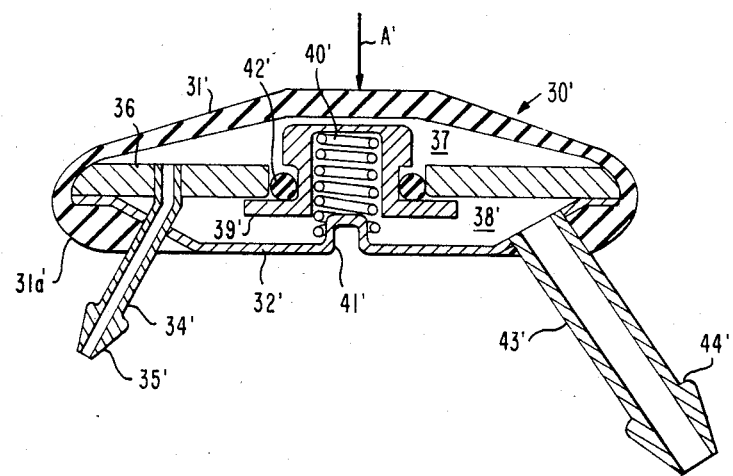
FIG. 7 is a cross-sectional view of an alternative embodiment of the releaser of the subject invention.

FIG. 7 illustrates a releaser 30' which is an alternative embodiment to the releaser 30 of FIG. 4. The releaser 30' operates similarly to releaser 30 except that the inlet tube 34' enters the upper chamber 37' and the outlet tubes 43' communicate with the lower chamber 38'. An additional change is that the "O"-ring 42' seals against an interior diameter of the base plate 36' as opposed to sealing against a bottom surface of the base plate 36 as shown in FIG. 4. With the construction of FIG. 7, pushing at A' will cause the pressurized working fluid to be promptly delivered to the stiffener cylinders. However, contrary to the releaser 30 design of FIG. 4, this design requires that the valve poppet 39' be pushed for instance with one or two fingers of one hand, while the penis is simultaneously squeezed, with for instance the other hand.

Various other modifications, adaptations and alternative designs are, of course, possible in light of the above teachings. Therefore, it should be understood at this time that within the scope of the appended claims, the invention may be practiced otherwise than as specifically described herein.

Having thus set forth the nature of the invention, what is claimed is:

1. An implantable apparatus for implantation at a selected site in a body comprising:

at least one distensible member for implantation, each of said at least one distensible members forming an internal chamber, each of said at least one distensible members being distensible when the respective said internal chambers thereof are pressurized;

pressure reservoir means;

valve means, said valve means coupling the respective said internal chambers of each of said at least one distensible members to said pressure reservoir, each of said at least one distensible members not being in communication with said pressure reservoir when said valve means is at rest, each of said at least one distensible members and said pressure reservoir being in communication when said valve means is opened;

a working fluid, said working fluid being disposed in said pressure reservoir means and being transferable between said internal chambers of each of said at least one distensible members and said pressure reservoir means; and fluid pressure generator means for inherently pressurizing said working fluid in said pressure reservoir means when said valve means is at rest, opening of said valve means causing a transfer of said working fluid from said pressure reservoir means to said internal chambers of each of said at least one distensible members.

2. An implantable apparatus in accordance with claim 1, further comprising working fluid adjustment means for permitting the adjustment of the volume of said working fluid subsequent to the implantation of said implantable apparatus in said body.

3. An implantable apparatus in accordance with claim 2, wherein said working fluid adjustment means comprises a septum mounted in contact on one side thereof with said working fluid, the other side thereof being accessable to a hypodermic needle.

4. An implantable apparatus in accordance with claim 2, wherein said valve means comprises a housing, said septum being mounted on said housing.

5. An implantable apparatus in accordance with claim 1, wherein said fluid pressure generator means comprises a variable volume enclosure disposed within said pressure reservoir and a pressurant fluid disposed within said variable volume enclosure, said pressurant fluid expanding in volume as said variable volume enclosure is permitted to expand.

6. An implantable apparatus in accordance with claim 5, wherein said pressurant fluid changes state between a gas and a liquid as said variable volume enclosure is permitted to expand and is forced to contract.

7. An implantable apparatus in accordance with claim 5, wherein said expandable enclosure comprises a closed ended bellows.

8. An implantable apparatus in accordance with claim 5, wherein said pressure reservoir includes a rigid housing.

9. An implantable apparatus in accordance with claim 5, wherein manual squeezing of each of said at least one distensible members forces said working fluid through said valve means, if in an open condition, into said pressure reservoir and causes compression of said variable volume enclosure, opening of said valve means permitting the forcing of said working fluid into each of said at least one distensible members under pressure of the expansion of said variable volume enclosure.

10. An implantable apparatus in accordance with claim 1, wherein said valve means is of the normally closed spring urged reciprocating poppet type.

11. An implantable apparatus in accordance with claim 9, wherein said manual squeezing of each of said at least one distensible members forces said valve means into an open condition under pressure of said working fluid.

12. An implantable apparatus in accordance with claim 8, further comprising working fluid adjustment means for permitting the adjustment of the volume of said working fluid subsequent to the implantation of said implantable apparatus in said body.

13. An implantable apparatus in accordance with claim 11, wherein said valve means comprises a housing, said working fluid adjustment means comprising a septum mounted on said housing such that one side thereof is in contact with said working fluid, the other side thereof being accessable to a hypodermic needle.

14. An implantable apparatus in accordance with claim 1, wherein said valve means comprises a housing, said housing including an external concave surface to improve the implanted positional stability thereof when said valve means is manually opened.

15. An implantable apparatus for achieving penile erection in a human male comprising:

at least one distensible cylinder for implantation in one of the corpora cavernosa of the penis of said human male, each of said at least one distensible cylinders forming internal chambers, each of said at least one distensible cylinders being distensible when the respective said internal chambers thereof are pressurized;

pressure reservoir means;

valve means, said valve means coupling the respective said internal chambers of each of said at least one distensible cylinders to said pressure reservoir, each of said at least one distensible cylinders not being in communication with said pressure reservoir when said valve means is at rest, each of said at least one distensible cylinders being in communication with said pressure reservoir when said valve means is opened;

a working fluid, said working fluid being disposed in said pressure reservoir means and being transferable between said internal chambers of each of said at least one distensible cylinders and said pressure reservoir means; and fluid pressure generator means for inherently pressurizing said working fluid in said pressure reservoir means when said valve means is at rest, opening of said valve means causing a transfer of said working fluid from said pressure reservoir means to said internal chambers of each of said at least one distensible cylinders.

16. An implantable apparatus in accordance with claim 15, wherein said at least one distensible cylinders comprise first and second distensible cylinders, said first distensible cylinder for implantation in one of the corpora cavernosa of said penis of said human male, said second distensible cylinder for implantation in the other of the corpora cavernosa of said penis of said human male.

17. An implantable apparatus in accordance with claim 15, further comprising working fluid adjustment means for permitting the adjustment of the volume of said working fluid subsequent to the implantation of said implantable apparatus in said human male.

18. An implantable apparatus in accordance with claim 17, wherein said working fluid adjustment means comprises a septum mounted in contact on one side thereof with said working fluid, the other side thereof being accessible to a hypodermic needle.

19. An implantable apparatus in accordance with claim 17 wherein said valve means comprises a housing, said septum being mounted on said housing.

20. An implantable apparatus in accordance with claim 15, wherein said fluid pressure generator means comprises a variable volume enclosure disposed within said pressure reservoir and a pressurant fluid disposed within said variable volume enclosure, said pressurant fluid changing state between a gas and a liquid respectively as said variable volume enclosure is permitted to expand and is forced to contract.

21. An implantable apparatus in accordance with claim 20, wherein said pressurant fluid changes state between a gas and a liquid as said variable volume enclosure is permitted to expand and is forced to contract.

22. An implantable apparatus in accordance with claim 20, wherein said expandable enclosure comprises a closed ended bellows.

23. An implantable apparatus in accordance with claim 20, wherein said pressure reservoir includes a rigid housing.

24. An implantable apparatus in accordance with claim 20, wherein manual squeezing of each of said at least one distensible cylinders forces said working fluid through said valve means into said pressure reservoir and causes compression of said variable volume enclosure, opening of said valve means permitting the forcing of said working fluid into each of said at least one distensible cylinders under pressure of the expansion of said variable volume enclosure.

25. An implantation apparatus in accordance with claim 15, wherein said valve means is of the normally closed spring urged reciprocating poppet type.

26. An implantable apparatus in accordance with claim 25, wherein said manual squeezing of each of said at least one distensible members forces said valve means into an open condition under pressure of said working fluid.

27. An implantable apparatus in accordance with claim 24, further comprising working fluid adjustment means for permitting the adjustment of the volume of said working fluid subsequent to the implantation of said implantable apparatus in said human male.

28. An implantable apparatus in accordance with claim 27, wherein said valve means comprises a housing, said working fluid adjustment means comprising a septum mounted on said housing such that one side thereof is in contact with said working fluid, the other side thereof being accessible to a hypodermic needle.

29. An implantable apparatus in accordance with claim 15, wherein said valve means comprises a housing, said housing including an external concave surface to improve the implanted positional stability thereof when said valve means is manually opened.

30. A method for permitting a human male to selectively achieve a penile erection comprising the steps of:
implanting in a human male first and second distensible cylinders, respectively, in the two corpora cavernosa of the penis of said human male, said distensible cylinders being distensible when supplied internally with a pressurized working fluid; and
simultaneously implanting in said human male a pressure reservoir and pressure means for inherently pressurizing a working fluid in said pressure reservoir, said distensible cylinders being in communication with said pressure reservoir through an also simultaneously implanted valve means;
opening of said valve means causing flow of said working fluid from said pressure reservoir to the interiors of said distensible cylinders so as to cause a pressure increase therein and distension of said distensible cylinders.

31. A method in accordance with claim 30, wherein said distensible cylinders are implanted such that they extend to a position just anterior of the pubic bone of said human male.

32. A method in accordance with claim 30, wherein said pressure reservoir and said pressure means are implanted in the abdomen of said human male.

33. A method in accordance with claim 30, wherein said valve means is implanted in said human male in a position where said valve means is readily accessible for manipulation.

34. A method in accordance with claim 30, further comprising the step of manually compressing said distensible cylinders to force said working fluid back into said pressure reservoir.

35. A method in accordance with claim 34, further comprising the step of activating said valve means during said last recited step.

36. A method in accordance with claim 34, wherein forcing said working fluid back into said pressure reservoir repressurizes said pressure means.

* * * * *

UNITED STATES PATENT AND TRADEMARK OFFICE
CERTIFICATE OF CORRECTION

PATENT NO. : 4,596,242

DATED : June 24, 1986

INVENTOR(S) : Robert E. Fischell

It is certified that error appears in the above-identified patent and that said Letters Patent is hereby corrected as shown below:

In the Specification

Column 1, line 26; delete "schlerosis" and insert therefor --sclerosis--.

Column 1, line 32; delete "patient" and insert therefor --patent--.

Column 3, line 56; delete "a" and insert therefor --an--.

Column 3, line 60; after "disadvantages" insert --,--.

Column 8, line 30; delete "lows,".

Signed and Sealed this

Thirtieth Day of September 1986

[SEAL]

Attest:

DONALD J. QUIGG

Attesting Officer

Commissioner of Patents and Trademarks